(12) United States Patent  (10) Patent No.: US 8,771,288 B2
Griego et al.  (45) Date of Patent: *Jul. 8, 2014

(54) MEDICAL DEVICE HAVING LINEAR TO ROTATION CONTROL

(71) Applicant: Boston Scientific Scimed, Inc., Maple Grove, MN (US)

(72) Inventors: John Griego, Blackstone, MA (US); Yem Chin, Burlington, MA (US); Gary McAlister, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/779,894

(22) Filed: Feb. 28, 2013

(65) Prior Publication Data

US 2013/0158562 A1  Jun. 20, 2013

Related U.S. Application Data

(63) Continuation of application No. 12/838,944, filed on Jul. 19, 2010, now Pat. No. 8,388,629, which is a continuation of application No. 10/447,261, filed on May 29, 2003, now Pat. No. 7,758,591, which is a continuation of application No. 09/870,683, filed on Jun. 1, 2001, now Pat. No. 6,602,262.

(60) Provisional application No. 60/253,723, filed on Nov. 29, 2000, provisional application No. 60/208,468, filed on Jun. 2, 2000.

(51) Int. Cl.
    *A61B 17/32*  (2006.01)
(52) U.S. Cl.
    USPC .......................................... 606/113; 606/110

(58) Field of Classification Search
    USPC ......... 606/108, 110–114, 127, 128, 167, 170, 606/191, 194, 205–209
    See application file for complete search history.

(56) References Cited

U.S. PATENT DOCUMENTS

| | | | |
|---|---|---|---|
| 1,174,379 A | 3/1916 | Bacon | |
| 4,209,019 A | 6/1980 | Dutcher et al. | |
| 4,739,838 A | 4/1988 | Marks | |
| 4,771,773 A | 9/1988 | Kropf | |
| 4,944,740 A * | 7/1990 | Buchbinder et al. | 606/194 |
| 4,979,951 A | 12/1990 | Simpson | |
| 5,020,545 A | 6/1991 | Soukup | |
| 5,129,913 A | 7/1992 | Ruppert | |
| 5,215,090 A | 6/1993 | Hon et al. | |
| 5,269,757 A * | 12/1993 | Fagan et al. | 604/95.01 |

(Continued)

*Primary Examiner* — Kathleen Holwerda
(74) *Attorney, Agent, or Firm* — Seager, Tufte & Wickhem, LLC

(57) ABSTRACT

A medical instrument converts linear movement of a shaft at a proximal end of the instrument to a rotational movement of an end effector of the instrument. According to one embodiment, the medical instrument includes an end effector formed of a snare loop connected to a shaft that is located within a sleeve. Once the sleeve is located near a desired location within a patient, the snare loop may be rotationally positioned with linear movement of the shaft by the operator. The shaft is formed with a threaded portion that matches threads formed in a torque transmitter element fixed within the sleeve. Linear movement of the shaft through the torque transmitter element causes the shaft to rotate. The medical instrument may also include a pivot connector for reducing torque build-up of the shaft and/or a clutch assembly for restricting controlled rotation of the snare loop to only one direction.

9 Claims, 3 Drawing Sheets

(56) References Cited

U.S. PATENT DOCUMENTS

| | | |
|---|---|---|
| 5,417,703 A | 5/1995 | Brown et al. |
| 5,472,439 A | 12/1995 | Hurd |
| 5,507,726 A | 4/1996 | Johnson et al. |
| 5,746,760 A * | 5/1998 | Humphrey, Jr. ............ 606/171 |
| 5,810,869 A * | 9/1998 | Kaplan et al. ............ 606/194 |
| 5,820,594 A | 10/1998 | Fontirroche et al. |
| 5,827,316 A | 10/1998 | Young et al. |
| 5,911,722 A | 6/1999 | Adler et al. |
| 5,947,978 A | 9/1999 | Holsinger |
| 5,964,777 A | 10/1999 | Drucker |
| 6,015,415 A | 1/2000 | Avellanet |
| 6,033,375 A | 3/2000 | Brumbach |
| 6,090,129 A | 7/2000 | Ouchi |
| 6,235,026 B1 | 5/2001 | Smith |
| 6,258,101 B1 | 7/2001 | Blake, III |
| 6,264,663 B1 | 7/2001 | Cano |
| 6,352,539 B1 | 3/2002 | Avellanet |
| 6,371,963 B1 | 4/2002 | Nishtala et al. |
| 6,517,539 B1 | 2/2003 | Smith et al. |
| 6,517,551 B1 | 2/2003 | Driskill |
| 6,602,262 B2 * | 8/2003 | Griego et al. ............ 606/113 |
| 7,758,591 B2 | 7/2010 | Griego et al. |

\* cited by examiner

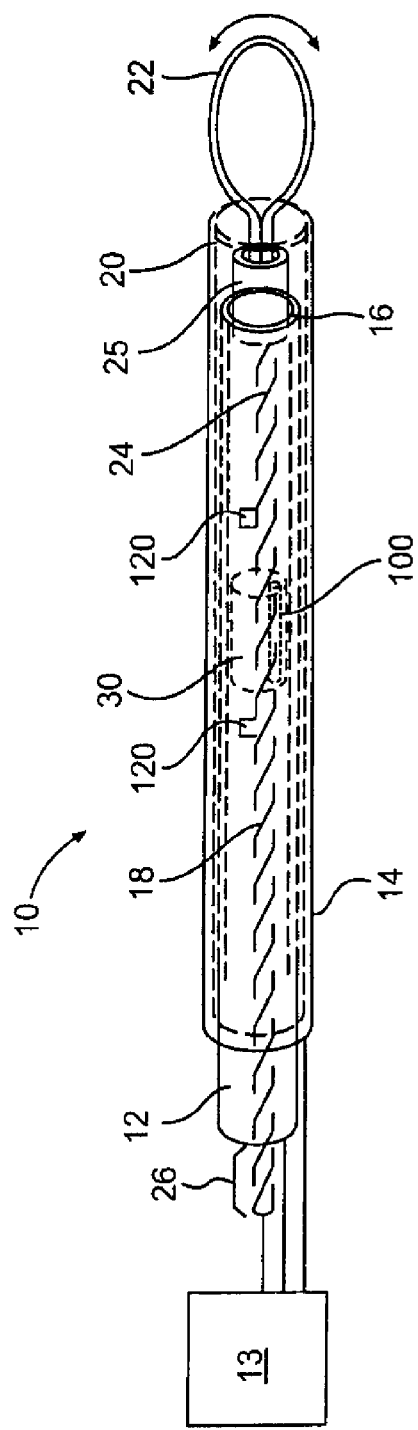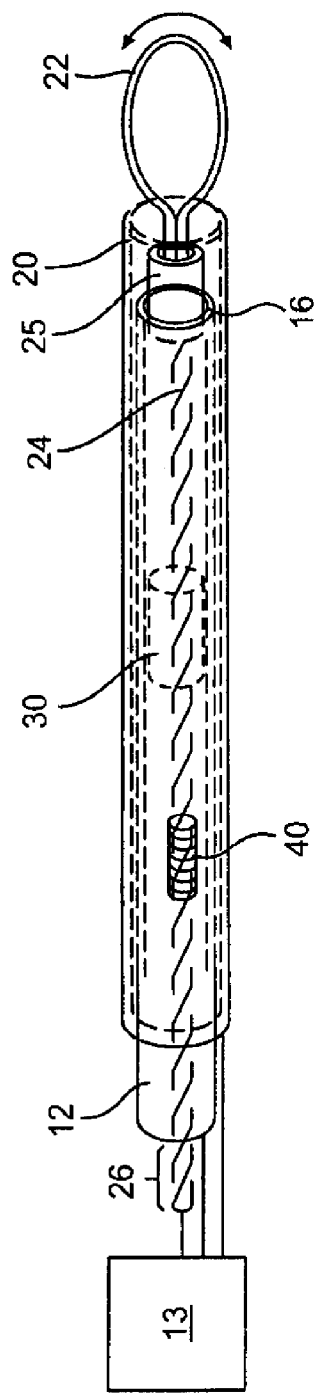

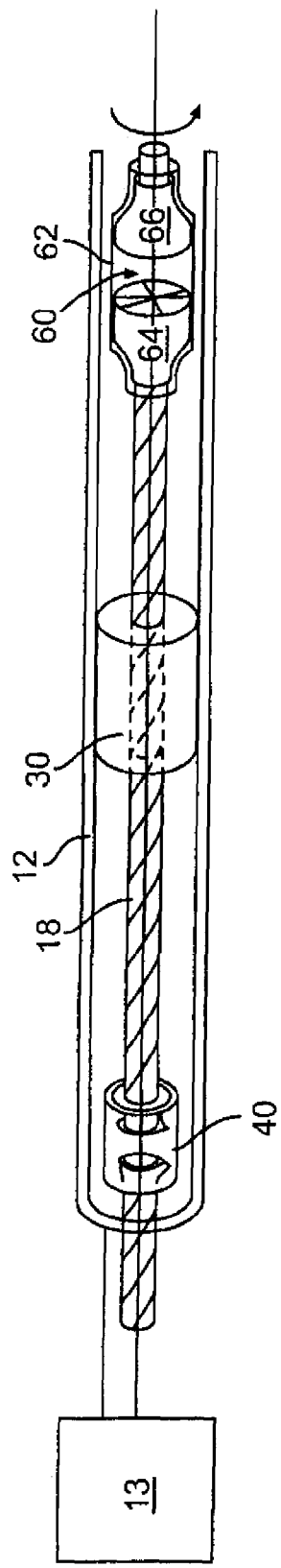
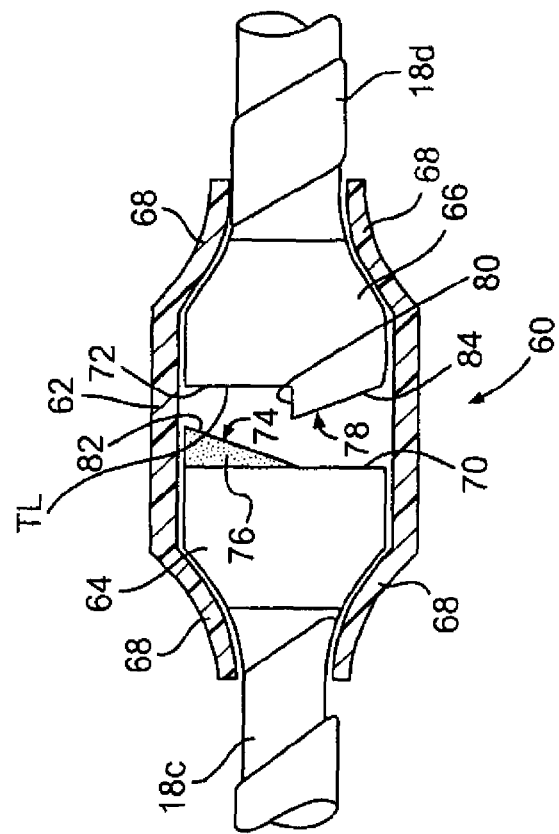

MEDICAL DEVICE HAVING LINEAR TO ROTATION CONTROL

This application is a continuation of U.S. application Ser. No. 12/838,944, filed Jul. 19, 2010, now U.S. Pat. No. 8,388,629, which is a continuation of U.S. application Ser. No. 10/447,261, filed May 29, 2003, now U.S. Pat. No. 7,758,591, which is a continuation of U.S. application Ser. No. 09/870,683, filed Jun. 1, 2001, now U.S. Pat. No. 6,602,262, which claims the benefit of U.S. Provisional Application No. 60/208,468, filed Jun. 2, 2000, and U.S. Provisional Application No. 60/253,723, filed Nov. 29, 2000, the entire disclosures of which are all incorporated herein by reference.

BACKGROUND OF THE INVENTION

1. Field of the Invention

The present invention relates to medical retrieval or electro-cutting devices, and more particularly to a medical retrieval or electro-cutting device including a rotatable end effector.

2. State of the Art

Medical retrieval or electro-cutting devices are used for a number of purposes within the body cavity. For example, a medical retrieval device in the form of a snare instrument is used for the endoscopic removal of hypertrophic tissue growths or polyps within a body cavity. Snare instruments generally include an elongated tubular member, such as a catheter sheath, a wire or shaft extending through the tubular member, and an elastic wire (e.g., stainless steel or Nitinol) forming a loop movable distally and proximally within the tubular member. The loop can be opened by moving the loop beyond the distal end of the tubular member and closed by retraction into the tubular member. Loop opening and closing is effected by movement of the shaft relative to the tubular member. A handle is provided at the proximal end of the instrument to facilitate this movement.

With the loop of the snare instrument in a retracted position, the distal end of the instrument is inserted through an endoscope into the gastrointestinal tract and moved toward a polyp or other tissue growth which is identified for removal from the wall of the tract. The handle of the instrument is then operated to expand the loop of the snare and an attempt is made to maneuver the loop to surround the polyp. If successful, the loop is then constricted about the polyp to excise it.

It will be appreciated that manipulation of the loop of the snare instrument about the polyp is a difficult, and sometimes unattainable, task. The expanded snare loop often lies in a plane which is not conducive for maneuvering about the target polyp. Therefore, the desired polyp retrieval often requires extensive effort, including attempts to rotate the catheter sheath to orientate the snare loop about the polyp. Rotation of the catheter sheath, however, often moves the snare loop out of position or causes detrimental whipping of the snare loop during the procedure.

SUMMARY OF THE INVENTION

The objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises a medical instrument including a sleeve having a proximal end and a distal end, a shaft at least partially received in the sleeve and including a proximal end and a distal end, an end effector connected to the shaft distal end, and a shaft portion having a discontinuous outer surface profile, a handle assembly attached to the proximal end of the sleeve and the proximal end of the shaft, the handle assembly capable of controlling at least a linear movement of the shaft, and a torque transmitter element fixedly located within the sleeve and having an opening extending therethrough for receiving the shaft portion, a surface of the opening having a discontinuous profile for mating with the discontinuous profile of the shaft portion so that a linear movement of the shaft causes a rotational motion of the end effector.

To achieve the objects and in accordance with the purpose of the invention, as embodied and broadly described herein, the invention further comprises a medical instrument including a sleeve having a proximal end and a distal end, a shaft formed of at least a first and second shaft segments, the shaft at least partially received in the sleeve and including a proximal end and a distal end, an end effector connected to the shaft distal end, and a shaft portion having a discontinuous outer surface profile, a handle assembly attached to the proximal end of the sleeve and the proximal end of the shaft, the handle assembly capable of controlling at least a linear movement of the shaft, a torque transmitter element fixedly located within the sleeve and having an opening extending therethrough for receiving the shaft portion, a surface of the opening having a discontinuous profile for mating with the discontinuous profile of the shaft portion so that a linear movement of the shaft causes a rotational motion of the end effector, and a pivot connector located within the sleeve and proximal to the torque transmitter element, the pivot connector including a housing for receiving a distal end of a first shaft segment and a proximal end of the second shaft segment, the housing substantially restricting relative linear movement of the first and second shaft segments while allowing unrestricted relative rotational movement of the first and second shaft segments.

To achieve the objects and in accordance with the purpose of the invention, as embodied and broadly described herein, the invention further comprises a medical instrument including a sleeve having a proximal end and a distal end, a shaft formed of at least a first and second shaft segments, the shaft at least partially received in the sleeve and including a proximal end and a distal end, an end effector connected to the shaft distal end, and a shaft portion having a discontinuous outer surface profile, a handle assembly attached to the proximal end of the sleeve and the proximal end of the shaft, the handle assembly capable of controlling at least a linear movement of the shaft, a torque transmitter element fixedly located within the sleeve and having an opening extending therethrough for receiving the shaft portion, a surface of the opening having a discontinuous profile for mating with the discontinuous profile of the shaft portion so that a linear movement of the shaft causes a rotational motion of the I end effector, and a clutch assembly located within the sleeve and distal of the torque transmitter element, the clutch assembly including a clutch housing for receiving a distal end of the first shaft segment and a proximal end of the second shaft segment, the housing restricting controlled rotational movement of the end effector to only one rotational direction.

To achieve the objects and in accordance with the purpose of the invention, as embodied and broadly described herein, the invention further comprises a method of positioning an end effector of a medical instrument at a desired location comprising the steps of positioning a sleeve within a patient the desired location, the sleeve including therein a shaft having the end effector connected to a distal end thereof; and moving a portion of the shaft in a linear direction through a torque transmitter element to cause rotation of the end effector to a desired rotational position.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description serve to explain the principles of the invention. In the drawings:

FIG. 1 is partial cross-section view of the medical device in accordance with a first embodiment of the present invention;

FIG. 3 is a partial cross-section view of the medical device in accordance with a second embodiment of the present invention;

FIG. 5 is a partial cross-section view of the medical device in accordance with a third embodiment of the present invention; and FIG. 6 is a partial cross-section view of the clutch assembly of the medical device in accordance with the third embodiment.

DETAILED DESCRIPTION OF THE INVENTION

Figure 2:
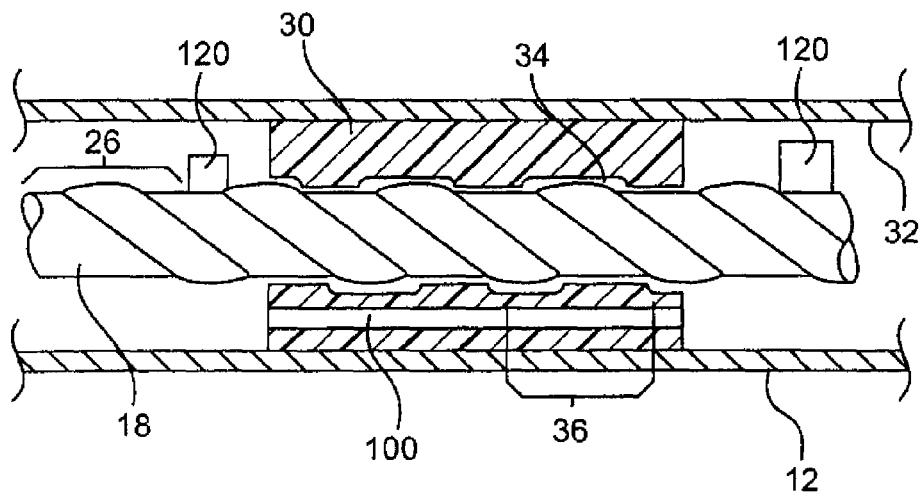
FIG. 2 is a partial cross-section view of the torque transmitter element of the medical device in accordance with the first embodiment.

Reference will now be made in detail to embodiments of the present invention, examples of which are illustrated in the accompanying drawings. Wherever possible, the same reference numbers will be used throughout the drawings to refer to the same or like parts.

FIG. 1 illustrates a medical device in the form of a medical snare instrument 10. While the present invention will be described in connection with a medical snare instrument 10, the invention may be applied to numerous other devices utilized during endoscopy or other surgical procedures. For example, the present invention could be applied with sphincterotomes or steerable catheters, and any one of a medical cutting instrument, such as, for example, a medical forceps instrument or a medical stone basket instrument.

Snare instrument 10 includes an inner elongated flexible tubular sleeve 12 and an outer elongated flexible tubular sleeve 14. Inner sleeve 12 is fixedly secured to a handle assembly (generically shown as element 13) and includes a proximal end (not shown) and a distal end 16. Inner sleeve 12 may be manufactured by an extrusion process and formed of thermoplastic material such as, for example, Nylon or Polyethylene. Other suitable materials known in the art may be used. A flexible wire or shaft 18 extends through inner sleeve 12, and inner sleeve 12 may be sized to fit closely to the wire and thereby eliminate excess play. Outer sleeve 14 also includes a proximal end (not shown) and a distal end 20, and is located outside of inner sleeve 12 so that it is movable relative to inner sleeve 12. Outer sleeve 14 may be manufactured by any suitable process and may be formed of any suitable material such as a fluoropolymer.

Shaft 18 is axially movable relative to inner and outer sleeves 12, 14 and includes a snare loop 22 mechanically coupled to its distal end 24. As will be discussed in more detail below, the proximal end of shaft 18 is connected to the handle assembly 13 for allowing the user to reciprocate shaft 18 relative to inner sleeve 12. The handle assembly is also connected to outer sleeve 14 for reciprocating outer sleeve 14 relative to both the inner sleeve 12 and shaft 18. Reciprocation of outer sleeve 14 relative to shaft 18 results in the snare loop 22 being contained within outer sleeve 14 or opened beyond the distal end 20 of outer sleeve 14. FIG. 1 shows snare loop 22 opened beyond the distal end 20 of outer sleeve 14.

Shaft 18 preferably includes a multifilament twisted and drawn or swaged cable. The filaments of the cable are preferably either stainless steel, nickel-titanium alloy, or a combination of the two. As shown in FIG. 2, the twists of cable forming shaft 18 create a discontinuous outer surface profile 26. In one embodiment of the invention, the discontinuous profile of shaft 18 forms a thread pattern about its peripheral surface, similar to that of a screw. Shaft 18 can be of other materials so long as it includes threads 26 and is flexible enough to bend, yet rigid enough to resist minor compressive forces.

Snare loop 22 is preferably also formed from a length of multifilament twisted and drawn or swaged cable, as described above, or another resilient cable or wire. The snare loop 22 is attached to the distal end 24 of the shaft 18, for example, by welding, soldering or crimping. Alternatively, the shaft may be formed from a resilient cable or wire which has first and second ends proximally twined and an untwined looped distal portion forming the snare loop; that is, the snare loop is integral with the shaft. As yet another alternative, the two sides of the snare loop may be formed from separate wire or cable elements coupled together at their proximal and distal ends to form the snare loop therebetween.

A positioning sleeve 25, or other suitable element, slidable within an inner surface 32 of the inner sleeve 12 may be attached about the junction of shaft 18 and snare loop 22. Positioning sleeve 25 thereby aids in ensuring a smooth, aligned movement of shaft 18. Accordingly, positioning sleeve 25 and inner sleeve 12 must be located such that positioning sleeve 25 does not extend completely beyond distal end 16 of the inner sleeve 12.

Inner sleeve 12 further includes a torque transmitter element 30 (FIG. 2) for converting linear movement of shaft 18 to rotational motion of the snare loop 22. Torque transmitter 30 is fixedly secured to the inner surface 32 of inner sleeve 12 and is generally cylindrically shaped with a port or opening 34 extending axially therethrough. Opening or port 34 includes a discontinuous surface profile, such as threads 36 having a pitch closely matching the outer surface profile or threads 26 of shaft 18. Accordingly, because torque transmitter 30 is fixed in inner sleeve 12, the mating of threads 26 of shaft 18 with threads 36 of port 34 during linear movement of the shaft 18 results in rotation of shaft 18 and snare loop 22. The pitch of the threads 26 of shaft 18 determines the sensitivity and magnitude of the rotation of snare loop 22 resulting from reciprocating of shaft 18. According to this embodiment of the present invention, threads 26 of shaft 18 are sized so that a maximum axial movement of shaft 18 at the handle assembly 13 causes a 360 degree rotation of snare loop 22 in one of a clockwise or counterclockwise direction. Conversely, maximum axial movement of shaft 18 in the opposite axial direction at the handle assembly causes a 360 degree rotation of snare loop 22 in the other of a clockwise or counterclockwise direction. Torque transmitter 30 may be formed of any suitable material and could be a separate element from the inner sleeve 12, or molded into the extrusion of the inner sleeve 12.

Certain endoscopic applications require injection of contrast media or other fluid into the body cavity to, for example, visualize the surgical site. To allow for injection of such fluid through inner sleeve 12, torque transmitter 30 may include small axial holes therethrough, such as, for example, opening 100, or grooves in its outer periphery. Torque transmitter 30 also may be formed of porous material that allows fluid to pass to the distal end of the device and into the body cavity. Alternatively, outer sleeve 14, a single lumen sleeve, could be replaced with a double lumen sleeve (not shown). With this configuration, one lumen would include all of the aspects described above and below in connection with outer sleeve 14, and the other lumen would form a passageway for injecting contrast media or other fluid to the desired site.

In a further embodiment of the present invention, a third sleeve (not shown) is included extending parallel to the exterior of outer sleeve 14. A distal end of the third sleeve merges with the interior area of outer sleeve 14 through a port in outer sleeve 14, the port being located between distal end 16 of inner sleeve 12 and distal end 20 of outer sleeve 14. With this configuration, the retrieval device can be guided into position at the desired site by inserting a guide wire through the third sleeve, through the outer sleeve port, and out distal end 20 of outer sleeve 14. Once the retrieval device is positioned at the desired site, the guide wire is removed from the third sleeve and the third sleeve is utilized to inject contrast media or other fluid to the desired site.

Handle assembly 13 may include a combined reciprocating control for both the outer sleeve 14 and shaft 18. Accordingly, the handle assembly includes a trigger element or other assembly for reciprocating outer sleeve 14 relative to shaft 18. Thus, activation of the trigger element causes snare loop 22 to either expand as the outer sleeve is retracted, so that snare loop 22 extends beyond the distal end of outer sleeve 14, or retract as outer sleeve 14 is urged over snare loop 22. The handle assembly may also include a thumb controlled element capable of reciprocation within the handle assembly. The thumb controlled element is directly connected to shaft 18 so that reciprocation of the thumb controlled element reciprocates shaft 18 through torque transmitter 30, and thereby rotates snare loop 22. A stop or stops 120 may be included on the shaft 18 or handle assembly 13 indicating the correspondence between linear movement of shaft 18 and rotational movement of snare loop 22. The handle assembly may also include locking mechanisms for fixing the position of both or either of shaft 18 and outer sleeve 14.

Figure 4:
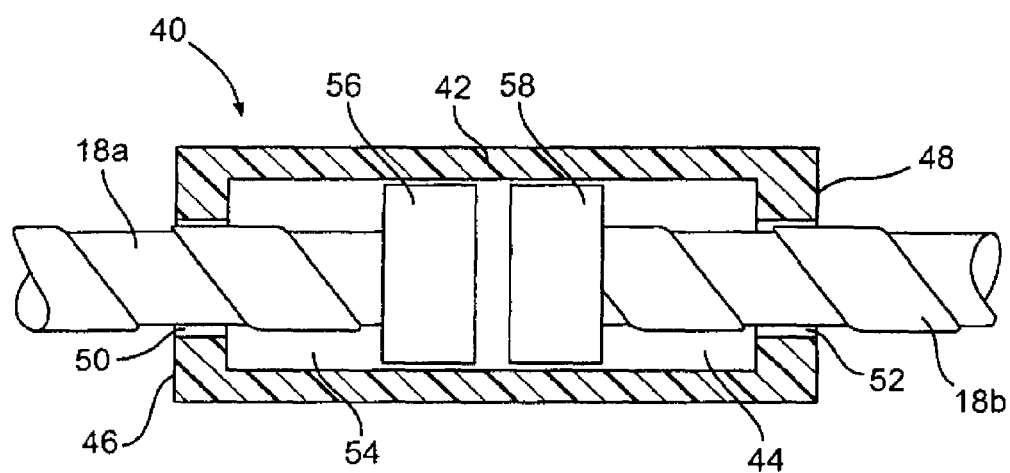
FIG. 4 is a partial cross-section view of the pivot element of the medical device in accordance with the second embodiment.

The thumb controlled element and shaft 18 may be fixedly secured together or the medical device may include a pivot connector for allowing shaft 18 to rotate without requiring rotation of the thumb controlled element. As illustrated in FIGS. 3 and 4, a pivot connector 40 can connect proximal and distal shaft segments 18a and 18b together to form shaft 18. Pivot connector 40 may be of any conventional arrangement and may include, for example, an outer body 42 having a bore 44 extending axially therethrough. The proximal and distal ends 46, 48 of pivot connector 40 include openings 50, 52 having a diameter smaller than a diameter of the central part 54 of bore 44. Central part 54 of bore 44 houses a distal end 56 of proximal shaft segment 18a and the proximal end 58 of distal shaft segment 18b. Proximal and distal segment ends 56 and 58 are each formed with an end element having diameters larger than the diameters of openings 48 and 50. The difference in diameters prohibits shaft segments 18a and 18b from being removed from pivot connector 40, but allows relative rotational motion between them.

Accordingly, movement of the proximal shaft segment 18a in a distal direction causes its end 56 to abut the proximal end 58 of distal segment 18b and force distal segment 18b to move in unison with proximal segment 18a. Also, movement of proximal shaft segment 18a in the proximal direction causes its distal end 56 to abut the proximal end 46 of pivot connector 40 and thereby force distal segment 18b in the proximal direction by its end's abutment against the distal end 48 of pivot connector 40. Accordingly, pivot connector 40 alleviates torque build-up in shaft 18 along the length of the medical device, and allows an operator to reciprocate shaft 18 at the handle assembly without any rotational movement In accordance with the present invention, distal end 20 of outer sleeve 14 may be reduced in diameter ("drawn down") to match the diameter of inner sleeve 12. The drawn down aspect of outer sleeve 14 would provide for improved positioning of snare loop 22 in relation to the desired polyp.

A user operating the above described embodiments of the present invention inserts the snare instrument 10, for example, into an endoscope located in the colon, utilizes the scope to identify for excision and retrieval a polyp on the wall of the colon, and maneuvers the distal end of the undeployed snare instrument in the colon to a location slightly beyond the polyp. The user then actuates the handle assembly of the instrument 10 to cause outer sleeve 14 to be moved proximally relative to the position of snare loop 22 to move the snare loop 22 out of outer sleeve 14. The snare loop 22 extends in axial relation to the axis of outer sleeve 14 and rests on or adjacent the wall of the colon proximal of the polyp. The snare loop 22 is then rotated into a desired position by reciprocal movement of the thumb controlled element of the handle assembly. The user then preferably advances outer sleeve 14, thereby tightly closing snare loop 22 about the polyp so that the polyp is excised. The outer sleeve 14 is then extended over snare loop 22 with polyp held therein, and the instrument 10 is removed from the colon.

While the snare instrument has been described for use in the gastrointestinal tract, it will be appreciated that it can be used elsewhere within the body, e.g., the uterus or urinary tract. It will therefore be appreciated by those skilled in the art that yet other modifications could be made to the provided invention without deviating from its spirit and scope as claimed.

FIGS. 5 and 6 illustrate yet another embodiment of the present invention. This embodiment is similar to the embodiments described above, except the outer sleeve 14 is removed and a clutch assembly 60 is added. In this embodiment snare loop 22 is configured so that it retracts into the same sleeve 12 that contains shaft 18, rather than an outer sleeve 14. Accordingly, a single reciprocation of shaft 18 can both rotate snare loop 22 when outside of sleeve 12 and retract snare loop 22 into sleeve 12. Clutch assembly 60 prohibits a rotation of shaft 18 from being transferred to snare loop 22 during retraction of the snare loop 22 into sleeve 12. Allowing a rotation of snare loop 22 only during the advancement of shaft 18 insures that snare loop 22 will maintain its position on the polyp during retraction of snare loop 22 in a proximal direction and into inner sleeve 12.

Clutch assembly 60 is located within sleeve 12 distal of torque transmitter element 30 and pivot connector 40, and includes a clutch body 62 for receiving a clutch proximal end element 64 connected to a distal end of proximal shaft segment 18c, and a clutch distal end element 66 connected to a proximal end of distal shaft segment 18d. Clutch body 62 may be of any conventional shape and material so long as it securely houses both clutch proximal end element 64 and clutch distal end element 66 and prevents those elements from being removed from body 62. For example, as illustrated in FIG. 6, clutch body 62 may be formed in a cylindrical shape with tapering ends 68. Further, clutch body 62 is sized to allow shaft segment 18c to rotate relative to shaft segment 18d. This relative rotation of shaft segments 18c and 18d can be provided by designing clutch body 62 with sufficient clearance to allow both clutch proximal end element 64 and clutch distal end element 66 to rotate within the housing without contacting each other, or by fixedly securing clutch distal end element 66 to clutch body 62 and providing sufficient clearance in clutch body 62 for clutch proximal end element 64 to rotate within body 62 without contacting clutch distal end element 66.

Clutch proximal end element 64 includes a distal face 70 having a gear configuration thereon. Similarly, clutch distal end element 66 includes a proximal face 72 having a gear configuration thereon. The gear configurations are designed so that when they mesh, rotation of proximal shaft segment 18c is transmitted to rotation of distal shaft segment 18d only in one direction, and not in the other rotational direction. This one-way only rotation of distal shaft segment 18d may be achieved by any standard unidirectional gearing arrangement. For example, distal face 70 of clutch proximal end element 64 could include at least one sloping protrusion 74. The slope of protrusion 74 provides an increasing thickness of protrusion 74 in the direction of the one-way movement and ends at a flat gearing face 76 extending perpendicular to distal face 70. Proximal face 72 of clutch distal end element 66 includes at least one sloping protrusion 78 similar and equal in number to that found on the clutch proximal end element 64. The slope of protrusion 78 of proximal face 72, however, provides an increasing thickness of protrusion 78 in the direction opposite of the one-way movement so that a flat gearing face 80 is formed to mesh with flat gearing face 76 only when flat gearing face 76 is rotated in the one-way direction.

In accordance with the embodiment of FIGS. 5 and 6, linear movement of shaft 18 in the distal direction at a handle assembly 13 is converted to linear and rotational movement at torque transmitter element 30. This conversion causes proximal shaft segment 18c and clutch proximal end element 64 to rotate and move distally within clutch body 62. Clutch proximal end element 64 moves distally within clutch body 62 until it contacts clutch distal end element 66. Upon contact with clutch distal end element 66, clutch proximal end element 66 continues to rotate relative to shaft segment 18d until flat gearing face 76 mates with flat gearing face 80. Upon mating of flat gearing faces 76, 80 shaft segments 18c and 18d rotate in unison in the direction of one-way movement, and thereby allow rotation of snare loop 22 to its desired rotational position. Once the target tissue is within snare loop 22, shaft 18 is retracted so that snare loop 22 is tightly closed about the polyp and snare loop 22 is urged into sleeve 12. This retraction of shaft 18 causes clutch proximal end element 64 to move in a proximal direction out of contact with clutch distal end element 66. Accordingly, rotation of proximal shaft segment 18c caused by torque transmitter element 30 during retraction of shaft 18 in the proximal direction does not cause rotation of distal shaft segment 18d and snare loop 22. Further, even before complete separation of clutch end elements 64 and 66, rotation of proximal shaft segment 18c during retraction of shaft 18 would not be transferred to segment 18d, but would only result in sliding contact of slope surfaces 82 and 84 of end elements 64 and 66.

As noted above, the embodiment of FIGS. 5 and 6 of the present invention includes a torque transmitter 30 and pivot connector 40 having the features detailed above. The medical device of FIGS. 5 and 6 may also include a handle assembly as described above, but without a reciprocating control for an outer sleeve. Further, the positioning sleeve 25 and additional sleeve or lumen described above could be incorporated into the embodiment of FIGS. 5 and 6.

Other embodiments of the invention will be apparent to those skilled in the art from consideration of the specification and practice of the invention disclosed herein. For example, as noted above, the snare loop described above could be replaced with a stone basket, cutting device, or other end effector requiring rotational movement. Further the outer surface of shaft 18 can be of any profile that will cause rotation of the shaft when reciprocated through the torque transmitter 30.

What is claimed is:

1. A method of positioning an end effector of a medical instrument at a desired location, the method comprising:
    positioning an assembly at a desired location within a patient's body, the assembly including:
    an outer sleeve;
    an inner sleeve disposed within the outer sleeve;
    a tubular member secured to an inner surface of the inner sleeve, the tubular member having a discontinuous inner surface and a discrete length extending from a first end to a second end of the tubular member, the discrete length of the tubular member disposed within the inner sleeve;
    a shaft at least partially disposed within the inner sleeve and disposed within the tubular member, the shaft including an end effector connected to a distal region thereof and having a discontinuous outer surface, the discontinuous outer surface being capable of interacting with the discontinuous inner surface of the tubular member;
    retaining the end effector within the outer sleeve during positioning of the assembly within the patient's body;
    moving a portion of the shaft in a distal linear direction relative to the outer sleeve such that the end effector exits a distal end of the outer sleeve; and
    moving a portion of the shaft in a linear direction relative to the inner sleeve causing the discontinuous inner surface of the tubular member to interact with the discontinuous outer surface of the shaft causing the end effector to rotate to a desired rotational position within the patient's body.

2. The method of claim 1, wherein the step of moving a portion of the shaft in a linear direction includes moving the portion of the shaft in a distal direction.

3. The method of claim 1, further comprising moving the shaft in a proximal direction while maintaining the rotational position of the end effector within the patient's body.

4. The method of claim 1, wherein the shaft includes a first shaft segment and a second shaft segment, and the step of moving a portion of the shaft in a linear direction causes rotation of only one of the first and second shaft segments.

5. The method of claim 1, further comprising moving the outer sleeve in a linear direction relative to the shaft to retract the end effector within a portion of the sleeve.

6. The method of claim 1, wherein the end effector comprises a snare loop.

7. The method of claim 1, wherein the assembly further comprises a clutch assembly for restricting rotational movement of the end effector to a single rotational direction.

8. The method of claim 1, wherein the assembly further comprises a pivot connector, the pivot connector substantially restricting relative linear movement between a first segment and a second segment of the shaft while allowing for unrestricted rotational movement between the first segment and the second segment of the shaft.

9. The method of claim 1, wherein the tubular member has a continuous outer surface opposite the discontinuous inner surface.

\* \* \* \* \*